United States Patent [19]

McCarthy

[11] Patent Number: 4,574,806
[45] Date of Patent: Mar. 11, 1986

[54] TUNNELLING DEVICE FOR PERIPHERAL VASCULAR RECONSTRUCTION
[75] Inventor: Brian D. McCarthy, Miami, Fla.
[73] Assignee: Cordis Corporation, Miami, Fla.
[21] Appl. No.: 656,798
[22] Filed: Oct. 1, 1984
[51] Int. Cl.⁴ .............................................. A61B 17/11
[52] U.S. Cl. ............................. 128/334 R; 128/303 R
[58] Field of Search ............... 128/334 R, 334 C, 335, 128/303 R, 4; 604/264, 280

[56] References Cited
U.S. PATENT DOCUMENTS

| | | | |
|---|---|---|---|
| 2,788,787 | 4/1957 | Trace | 128/303 R |
| 3,710,777 | 1/1973 | Sparks | 128/1 R |
| 3,866,247 | 2/1975 | Sparks | 3/1 |
| 3,866,609 | 2/1975 | Sparks | 128/303 R |
| 3,958,557 | 5/1976 | Sharp et al. | 128/303 R X |
| 3,999,551 | 12/1976 | Spitz et al. | 128/303 R |
| 4,327,722 | 5/1982 | Groshong et al. | 128/214.4 |
| 4,418,693 | 12/1983 | LeVeen et al. | 128/303 R |
| 4,431,426 | 2/1984 | Groshong et al. | 604/280 |
| 4,432,752 | 2/1984 | Marlon | 604/53 |
| 4,487,567 | 12/1984 | Possis et al. | 425/403 |
| 4,509,516 | 4/1985 | Richmond | 128/303 R |

FOREIGN PATENT DOCUMENTS 610530  6/1978  U.S.S.R. ........................... 128/334 R

Primary Examiner—William H. Grieb
Attorney, Agent, or Firm—Henry W. Collins; Thomas R. Vigil

[57] ABSTRACT

A tunnelling device for use in the placement of a peripheral cardiovascular graft in a living body comprising three portions. The first portion is a hollow curved conduit forming portion having a distal end, a proximal end and an interior lumen. The second portion is a hollow bullet shaped nose section releasably engageable with the distal end of the conduit forming portion. The third portion is a handle which is releasably locked to the proximal end of the conduit forming portion and has a stylet which is fixed to and extends distally from the handle, the stylet being received within and through the lumen of the conduit forming portion and terminating at a position within the nose section.

19 Claims, 9 Drawing Figures

TUNNELLING DEVICE FOR PERIPHERAL VASCULAR RECONSTRUCTION

BACKGROUND OF THE INVENTION

1. Field of the Invention

The present invention relates to a tunnelling device for use in forming an anatomical tunnel within which is to be received a cardiovascular graft during reconstructive peripheral vascular surgery. More specifically, the invention relates to a tunnelling device which is a combined tunneller, graft introducing device and temporary conduit for use in the placement of a vascular graft within tissue prior to the fixation of the graft to an existing peripheral vessel to form a bypass around a vessel or portion thereof.

2. Description of the Prior Art

When performing peripheral vascular reconstructive procedures, it is a common practice to create a subcutaneous or anatomic tunnel between anastomotic sites for passage of a graft therethrough. The graft may be of autogenous, synthetic or biological origin.

Synthetic grafts are relatively durable and may be pulled through an anatomic tunnel without damage. However, grafts of biological origin are relatively fragile, whether autografts, heterografts or homografts, and can tear if pulled through an antomic tunnel. To minimize chances of tearing of the graft due to inherent friction between the graft and surrounding tissue, surgeons have provided a conduit, such as a disposable chest tube container, around the tunnelling device for the formation of a subcutaneous conduit through which the graft is to be passed once the tunnelling device is removed. After the graft is fed through the conduit forming container, the container is removed with the graft remaining in the anatomic tunnel.

Various prior art devices have been proposed for assisting the passage of a tubular element through body tissue. Examples of some of these devices are disclosed in the following U.S. Patents:

| U.S. Pat. No. | PATENTEE |
| --- | --- |
| 3,710,777 | Sparks |
| 3,866,247 | Sparks |
| 3,866,609 | Sparks |
| 3,999,551 | Spitz et al. |
| 4,327,722 | Groshong et al. |
| 4,418,693 | Leveen et al. |
| 4,431,426 | Groshong et al. |
| 4,432,752 | Marlon |

The Sparks U.S. Pat. No. 3,710,777 discloses a slightly bent metal tunnelling tube containing a flexible plastic core rod which closes off the distal end of the tube with a plug provided on the rod. Once the tunnelling tube and core rod have been placed in a thigh of a patient, the core rod is removed. A mandrel assembly with a coarse mesh fabric coating is inserted into the tunnelling tube. The tunnelling tube is then removed, leaving the mandrel assembly in place, around which a graft is grown.

The Sparks U.S. Pat. Nos. 3,866,247 and 3,866,609 disclose a similar tunnelling tube for different processes of graft formation.

The Spitz et al. U.S. Pat. No. 3,999,551 discloses a subcutaneous guide assembly comprising an elongated rod of predetermined contour and length which has a handle on one end and to the other end of which a variety of surgical elements can be threadedly engaged. In use, the assembly is inserted into one incision and then the distal end is caused to exit a second incision. At that time, the surgical element is attached to the distal end and pulled back into the body for implantation of the device.

The Groshong et al. U.S. Pat. Nos. 4,327,722 and 4,431,426 disclose apparatus for intravenous therapy such as total parenteral provision of nourishment. For long term use, a passer for a catheter of the assembly is provided which passer comprises a sharp tipped elongate tube.

The LeVeen et al. U.S. Pat. No. 4,418,693 discloses a vein and tubing passer. The passer comprises inner and outer slidable tubular members. One is flexible and the other is rigid. Once placed, the rigid member is withdrawn and a grafting element is attached to the flexible member which pulls the grafting element through the body tissue to the desired location.

The Marlon U.S. Pat. No. 4,432,752 discloses a procedure for inserting indwelling catheters. A larger catheter is utilized to provide a tunnel for a smaller catheter.

As will be described in greater detail hereinafter, the tunnelling device of the present invention differs from the previously proposed devices by providing in a single unit, all the elements necessary for the atraumatic placement of a graft within an anatomic tunnel thereby to minimize the possibility of damage to the graft.

SUMMARY OF THE INVENTION

According to the invention there is provided a tunnelling device for use in the placement of a peripheral cardiovascular graft in a living body comprising: a hollow curved conduit forming portion having a distal end and a proximal end and an interior lumen; a hollow bullet shaped nose section releasably engageable with said distal end of said conduit forming portion; a handle which is releasably locked to the proximal end of said conduit forming portion; and a stylet which is fixed to and extends distally from said handle, said stylet being received within and through said lumen of said conduit forming portion and terminating at a position within said nose section.

Further according to the invention there is provided a method for utilizing the tunnelling device comprising the steps of: forming two incisions distal and proximal to a chosen area of anastomosis; inserting the tunnelling device in the primary incision and performing blunt dissection of tissue between the two incisions with the nose section of the tunnelling device; removing the nose section from the conduit forming portion once the nose section exits the second incision; attaching a graft to the stylet proximal to the tip thereof and unlocking the handle from the conduit forming portion; retracting the handle proximally from the conduit forming portion thereby advancing the graft through the conduit forming portion until the graft and tip of the stylet exit the primary incision; releasing the graft from the stylet; holding the distal end of the graft while pulling the conduit forming portion out of the tissue through the primary incision from its proximal end; forming the anastomosis around the area of vasculature to be bypassed; and closing the incisions.

DESCRIPTION OF THE PREFERRED EMBODIMENT

Figure 1:
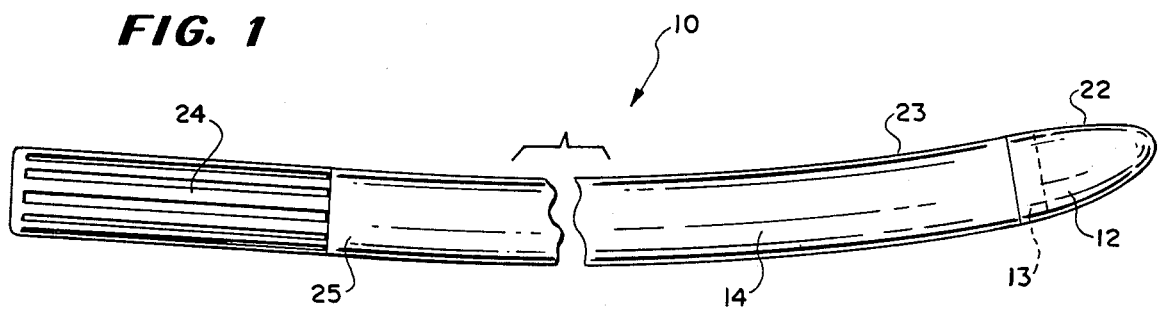
FIG. 1 is a side view of the tunnelling device of the present invention.

Referring now to the drawings in greater detail, there is illustrated in FIG. 1 a tunnelling device 10 which is utilized in the placement of a peripheral cardiovascular graft and which is constructed according to the teachings of the present invention. The tunnelling device 10 comprises three sections.

The first section is a nose section 12 which has an elliptical or bullet shape that facilitates blunt dissection inherent in the tunnelling procedure with minimal tissue trauma and resistance to passage, as opposed to tunnellers having spherical or rounded tips. The nose section 12 is approximately 2 inches long and is releasably, preferably threadedly, received on the distal end edge 13 of a conduit forming portion 14 which is the second section.

The conduit forming portion 14 as well as the nose portion preferably are made of ⅛ inch thick stainless steel or aluminum tubing with the conduit forming portion 14 having an outer diameter of approximately ¾ inch and an inner diameter of approximately ½ inch.

The conduit forming portion 14 is curved to facilitate passage of the tunnelling device 10 between incisions and enables a surgeon to guide the tunnelling device 10 from a first incision through tissue to a second incision as will be described in greater detail hereinafter.

The distal end edge 13 of the conduit forming portion, where it attaches to the nose section 12, is rounded at 18 to prevent damage to a tissue graft entering the conduit forming portion 14.

Also, the interior or lumen 20 of the conduit forming portion 14 is specially polished to reduce friction and possible consequent damage to the fragile tissue graft to be passed therethrough.

Additionally, the nose section 12 and conduit forming portion 14 are coated on the outer surfaces 22 and 23 with a low friction material, sold under the trademark Neadox, by a special process which results in reduced friction between the tunnelling device 10 and the host tissue when a tunnel is being formed with the device 10.

Figure 3:
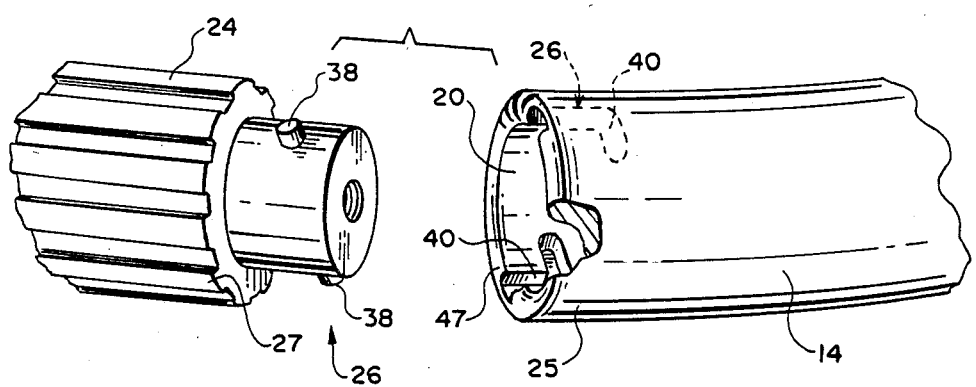
FIG. 3 is a side perspective view of a key mechanism or bayonet mount of the tunnelling device for detachably locking a proximal end of a hollow conduit forming portions of the device to a handle for the device.

A handle 24, which is the third section, and which is approximately 5 inches long, is fixed to a proximal end 25 of the curved conduit forming portion 14 by a bayonet latch structure 26 (FIG. 3).

The handle 24 is provided with knurling or ribbing 27 on its exterior surface to facilitate grasping thereof without slippage with a gloved hand during the surgical procedure.

The tunnelling device 10 is approximately 25 inches long and weighs approximately 5 pounds. The weight of the device 10 is an advantage during the tunnelling procedure as will be described in detail hereinafter.

Figure 2:
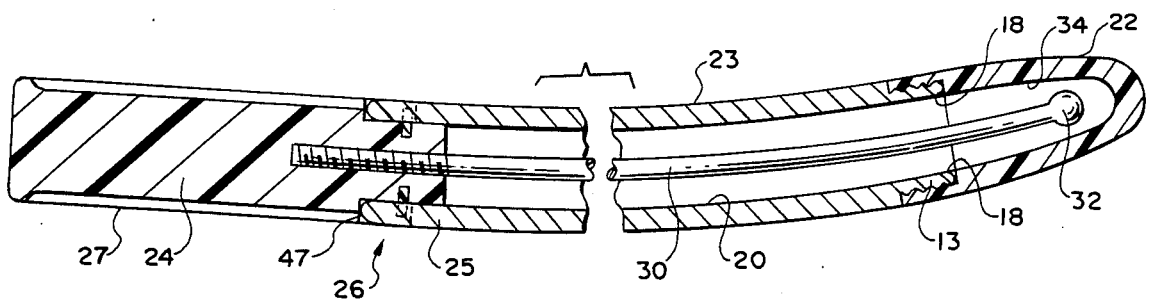
FIG. 2 is a longitudinal sectional view of the tunnelling device of the present invention shown in FIG. 1.

As shown in FIG. 2, the nose section 12 and conduit forming portion 14 are hollow while the handle 24 is solid. Extending axially from the center of the handle 24 is a stainless steel probe/stylet 30 having a ball tip 32. The diameter of the ball tip 32 is approximately 4 mm and can accomodate grafts of small inner diameter. The stylet 30 is preferably attached to the handle 24 by welding.

As shown, the stylet 30 is of sufficient length to be received through the lumen 20 of the conduit forming portion 14 and to terminate with the ball tip 32 being received within a cavity 34 of the nose section 12. The ball tip 32 is specially polished to prevent intraluminal damage to the graft when the graft is fed over the ball 32. The nose section 12 is threadedly engaged to the distal end 13 of the conduit forming portion 14 to ensure a positive, secure fit.

Referring to FIG. 3, the handle 24 is secured to the proximal end 25 of the conduit forming portion 14 by a bayonet latch structure 26 which comprises bayonet pins 38 on the handle 24 and a keeper slot 40 in the conduit forming portion 14 on each side of the tunnelling device 10.

Figure 4:
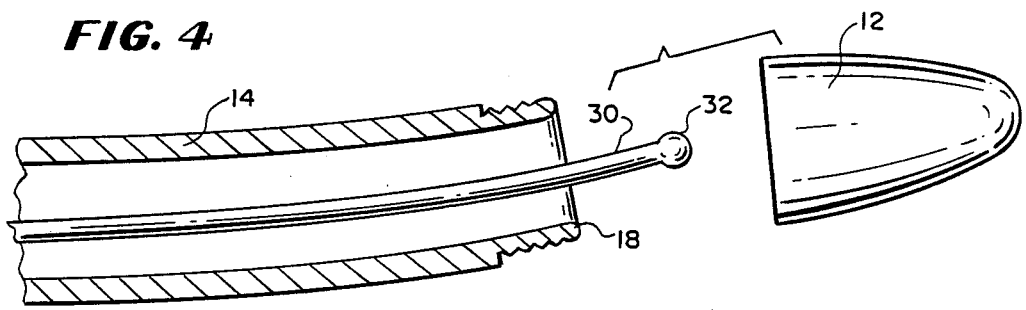
FIG. 4 is a sectional view of the tunnelling device shown in FIG. 1 and shows a hollow nose portion removed from the distal end of a hollow conduit forming portion of the device with a ball tip stylet located within a lumen of the device.

In FIG. 4, the nose section 12 is shown removed from the conduit forming portion 14. Here the ball tip 32 of the stylet 30 is shown extending from the distal end 13 of the conduit forming portion 14 of the device 10. The provision of the ball tip 32 for the stylet 30 provides for simple and atraumatic attachment of the graft to the stylet 30.

Figure 5:
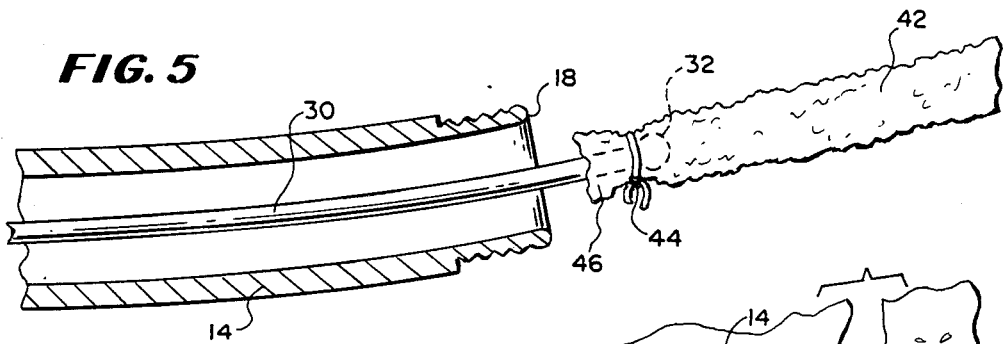
FIG. 5 is an enlarged sectional view of the conduit forming portion of the tunnelling device and shows a graft attached to the ball tip end of the stylet prior to the graft being pulled through the conduit forming portion.

In FIG. 5 is shown a graft 42 fixed to the stylet 30 by means of a suture 44 being placed through a proximal end portion 46 of the graft 42 which has been fed over the ball tip 32 of the stylet 30. The suture 44 is tied proximal of the ball tip 32 around the stylet 30 to keep the graft 42 from pulling free. An elastic loop may be used in place of the suture 44.

Figure 6:
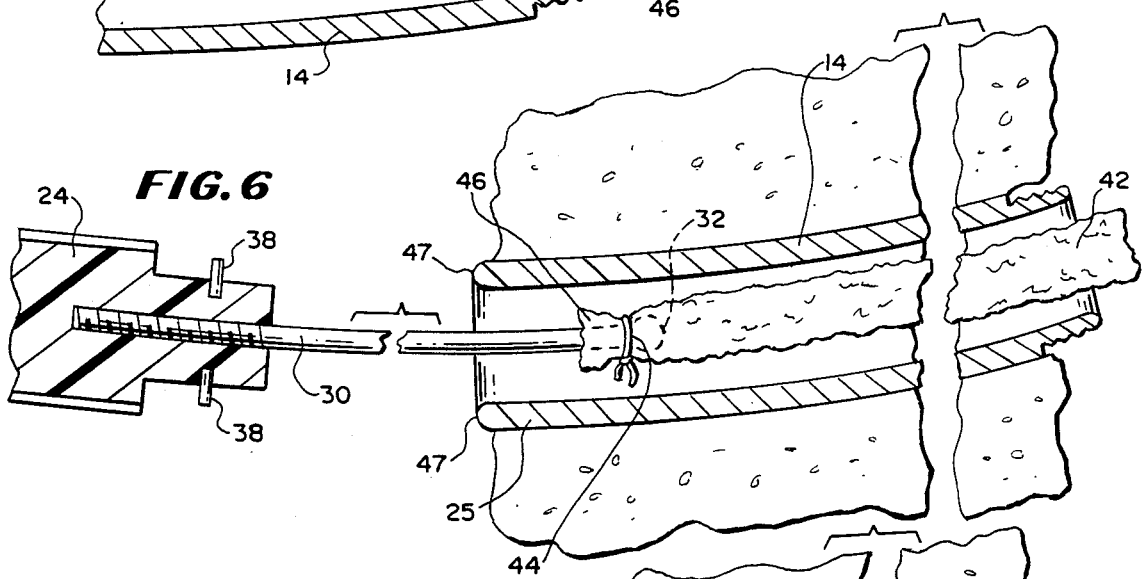
FIG. 6 is a sectional view of the tunnelling device of FIG. 5 in living tissue and shows the graft being pulled into the distal end of and through the lumen of the conduit forming portion.

By rotating the handle 24 it can be unlatched from the conduit forming portion 14 and by pulling it out and away from the conduit forming portion 14, as shown in FIG. 6, the graft 42 is advanced through the conduit forming portion 14 from its distal end 13 until it exits the proximal end 25 of the conduit forming portion 14 which is also rounded at 47.

Figure 7:
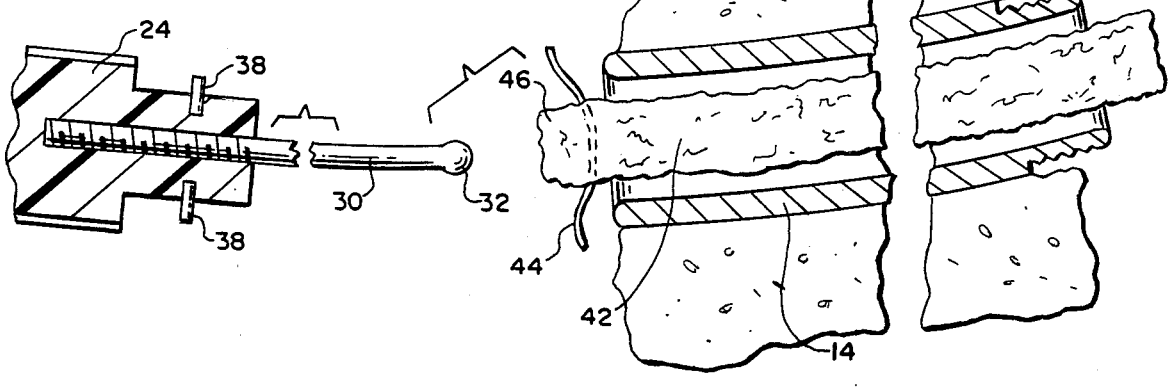
FIG. 7 is a sectional view of the conduit forming portion of the tunnelling device shown in FIG. 6 in living tissue and shows the end of the graft released from the stylet after the stylet has been pulled through the proximal end of the conduit forming portion.

As shown in FIG. 7, once the ball tip end 32 of the stylet 30 extends beyond the proximal end 25 of the conduit forming portion 14 with the attached end portion 46 of the graft 42 thereon, the suture 44 securing the graft 42 to the stylet 30 can be removed and the handle 24 is set aside.

Figure 8:
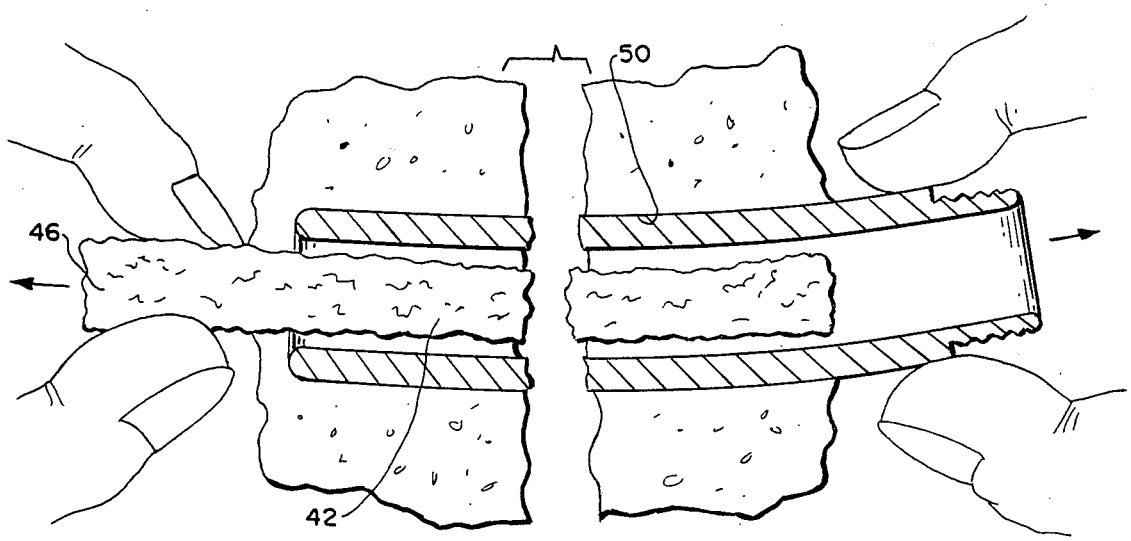
FIG. 8 is a sectional view of the tunnelling device shown in FIG. 7 and shows the conduit forming portion being removed from within a living tissue anatomic tunnel once the graft has been fed therethrough.
Figure 9:
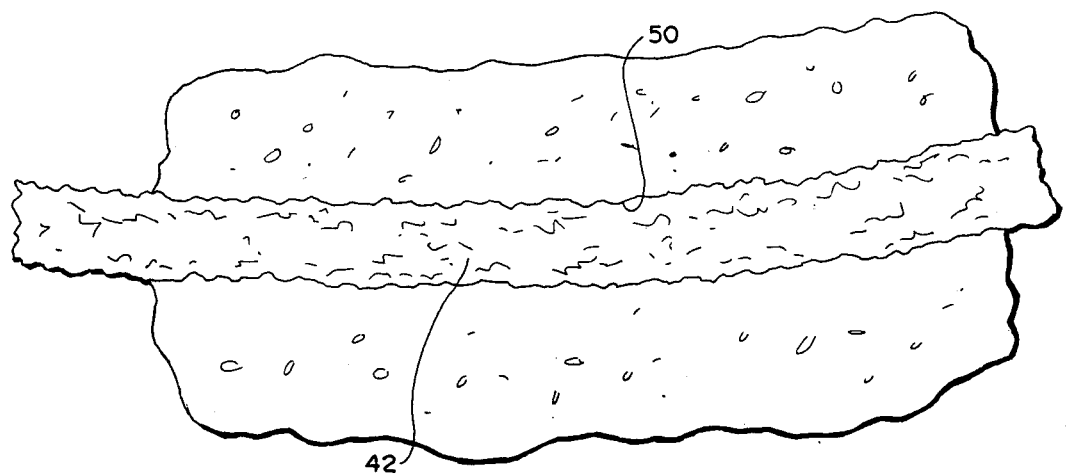
FIG. 9 is a lateral view of the graft received within the anatomic tunnel within the living tissue once the tunnelling device has been removed.

Now, as shown in FIG. 8, a surgeon holds the distal end 48 of the graft 42 exiting the distal end 13 of the conduit forming portion 14 and slowly pulls the conduit forming portion 14 out of a first or primary incision (not shown) leaving the graft 42 within the anatomic tunnel 50 as shown in FIG. 9.

In using the device 10 of the present invention, two incisions are first made through skin into underlying tissue, one incision proximal to and the other incision distal to the blood vessel or portion thereby to be by-passed.

The elliptically shaped nose section 12 of the tunnelling device 10 is then inserted into the primary incision. Pressure is applied to the handle 24 to force the tunnelling device further into the incision and blunt dissection is carried out to form the subcutaneous tunnel 50. The force or pressure applied is minimized by utilizing the weight of the device 10 to the surgeon's benefit. The subcutaneous tunnel 50 is formed in such a manner as to have the nose section 12 exit a second or secondary incision. The curved shape of the conduit forming portion 14 of the tunnelling device 10 facilitates directional control of the device to bring it through the secondary incision.

After the nose section 12 exits the secondary incision, it is unscrewed from the conduit forming portion 14 and set aside. The ball tip 32 of the stylet 30 now is exposed and extends out of the conduit forming portion 14. One end of the graft 42 to be utilized in the bypass is fed over the ball tip 32 of the stylet 30 and secured by a suture or elastic loop as shown in FIG. 4. Once the graft 42 is secured, the handle 24 is easily detached from the conduit forming portion 14 and retracted proximally from the conduit forming portion 14 simultaneously drawing the ball tip 32 of the stylet 30 into and through the conduit forming portion 14 drawing the graft through the lumen 20 of the conduit forming portion 14 as well. Once the graft has been drawn through the conduit forming portion 14, to the site of the primary incision, the suture or elastic loop 44 is released and the handle 24 is set aside.

The surgeon then holds the graft 42 in place by grasping the distal end thereof and removes the conduit forming portion 14 through the primary incision (FIG. 8), by grasping the proximal end 25 thereof and pulling slowly. The graft alone then remains within the anatomic or subcutaneous tunnel 50 (FIG. 9).

The surgeon now forms the anastomoses, one at each end of the graft 42 by suturing the graft 42 to the blood vessel at the desired locations, one end on either side of the area to be bypassed.

From the foregoing description, the device 10 of the present invention has a number of advantages, some of which have been described above and others of which are inherent in the invention. For example, the tunnelling device 10 of the present invention provides:

a. an atraumatic, low friction surface to reduce friction, resistance and tissue damage during the passage of the devide 10 through the tunnel 50;

b. a detachable, specially designed nose section 12 to reduce tissue trauma and resistance during passage and permitting easy access to the ball tip stylet 30 for attachment of the graft 42;

c. a tubular conduit forming portion 14 which has a rounded circumference and polished interior to reduce damage to the exterior of the graft 42 and which remains "in situ" during passage of the graft to eliminate the friction and possible damage to the graft 42 by bronchoscopy forceps or other traumatic devices as is often done when using other tunnelling devices; and e. In the case of long bypasses, the tunnelling device 10 may be reassembled for the purpose of accomplishing a second tunnelling procedure in like manner to the location of the secondary incision and anastomosis.

Also, modifications can be made to the tunnelling device 10 of the present invention without departing from the teachings of the present invention. Accordingly, the scope of the invention is only to be limited as necessitated by the accompanying claims.

I claim:

1. A tunnelling device for use in the placement of a peripheral cardiovascular graft in a living body comprising: a hollow curved conduit forming portion having a distal end, a proximal end and an interior lumen; a hollow bullet shaped nose section releasably engageable with said distal end of said conduit forming portion; a handle which is releasably locked to the proximal end of said conduit forming portion; and a stylet which is fixed to and extends distally from said handle, said stylet being received within and through said lumen of said conduit forming portion and terminating at a position within said nose section.

2. The tunnelling device of claim 1 wherein said nose section is made of stainless steel or aluminum tube.

3. The tunnelling device of claim 1 wherein said conduit forming portion is made of stainless steel or aluminum tube.

4. The tunnelling device of claim 1 wherein said handle is formed of stainless steel.

5. The tunnelling device of claim 1 wherein said stylet has a ball tip and is made of stainless steel.

6. The tunnelling device of claim 1 wherein said nose section and conduit forming portion are coated with a low friction material.

7. The tunnelling device of claim 1 wherein said lumen of said conduit forming portion is polished.

8. The tunnelling device of claim 1 wherein said stylet has a ball tip which is highly polished.

9. The tunnelling device of claim 1 wherein the distal circumferential edge of said conduit forming portion is rounded.

10. The tunnelling device of claim 1 having a weight of approximately 5 pounds.

11. The tunnelling device of claim 1 having a length of approximately 25 inches.

12. The tunnelling device of claim 1 having an outer diameter of approximately $\frac{3}{4}$ inch.

13. The tunnelling device of claim 1 having an inner diameter of approximately $\frac{1}{2}$ inch.

14. The tunnelling device of claim 1 wherein the thickness of the wall of the conduit forming portion is approximately $\frac{1}{8}$ inch.

15. The tunnelling device of claim 1 wherein the diameter of the ball tip of the stylet is approximately 4 mm.

16. The tunnelling device of claim 1 wherein said nose section is threadedly engageable with said conduit forming portion.

17. The tunnelling device of claim 1 wherein said handle is attached to said conduit forming portion by means of a bayonet latch structure.

18. The tunnelling device of claim 1 wherein said ball tip stylet is secured to said handle by welding.

19. A method for utilizing the tunnelling device of claim 1 comprising the steps of: forming two incisions proximal and distal to a chose area of anastomosis; inserting the tunnelling device in the primary incision and performing blunt dissection of tissue between the two incisions with the nose section of the tunnelling device; removing the nose section from the conduit forming portion once the nose section exits the second incision; attaching a graft to the stylet proximal to the tip thereof and unlocking the handle from the conduit forming portion; retracting the handle proximally from the conduit forming portion until the graft and tip of the stylet exit the primary incision; releasing the graft from the stylet; holding the distal end of the graft while pulling the conduit forming portion out of the tissue through the primary incision from its proximal end; forming the anastomoses around the area of vasculature to be bypassed; and closing the incisions.

* * * * *

Notice of Adverse Decision in Interference

In Interference No. 102,049, involving Patent No. 4,574,806, B. D. McCarthy, TUNNELLING DEVICE FOR PERIPHERAL VASCULAR RECONSTRUCTION, final judgment adverse to the patentee was rendered July 7, 1989, as to claims 1-19.

[*Official Gazette September 19, 1989.*]